United States Patent
Yu et al.

(10) Patent No.: US 9,834,592 B2
(45) Date of Patent: Dec. 5, 2017

(54) MODIFIED COLOSTRUM PROTEIN AND APPLICATION THEREOF

(71) Applicant: HUNG GUANG BIOTECH CO., LTD., Tainan (TW)

(72) Inventors: Tse-Min Yu, Tainan (TW); Hung-Shu Chang, Tainan (TW)

(73) Assignee: HUNG GUANG BIOTECH CO., LTD., Tainan (TW)

( * ) Notice: Subject to any disclaimer, the term of this patent is extended or adjusted under 35 U.S.C. 154(b) by 0 days.

(21) Appl. No.: 15/255,082

(22) Filed: Sep. 1, 2016

(65) Prior Publication Data

US 2017/0260256 A1    Sep. 14, 2017

(30) Foreign Application Priority Data

Mar. 14, 2016  (TW) .............. 105107814 A
Jul. 5, 2016   (TW) .............. 105121215 A

(51) Int. Cl.
*C07K 16/04* (2006.01)
*A61K 39/395* (2006.01)
*A23K 20/147* (2016.01)
*A23K 50/30* (2016.01)
*A61K 38/17* (2006.01)
*C07K 14/47* (2006.01)
*A61K 39/00* (2006.01)

(52) U.S. Cl.
CPC ............ *C07K 16/04* (2013.01); *A23K 20/147* (2016.05); *A23K 50/30* (2016.05); *A61K 38/1709* (2013.01); *A61K 39/39508* (2013.01); *C07K 14/47* (2013.01); *A61K 39/00* (2013.01); *A61K 2039/505* (2013.01); *A61K 2039/542* (2013.01); *C07K 2317/12* (2013.01)

(58) Field of Classification Search
CPC ................................ A61K 39/00; C07H 21/04
USPC .................. 424/184.1, 185.1; 536/23.1, 23.5
See application file for complete search history.

*Primary Examiner* — Rodney P Swartz
(74) *Attorney, Agent, or Firm* — AEON Law; Adam L. K. Philipp; Manasi Vakil

(57) ABSTRACT

Disclosed is a modified colostrum protein having an amino acid sequence shown in SEQ ID NO.: 1, which is generated by replacing Ile at position 33, Glu at position 101 and Arg at position 175 present in the amino acid sequence of a wild type colostrum protein shown in SEQ ID NO.: 2 respectively with Ala, Cys and Cys.

3 Claims, 5 Drawing Sheets

MODIFIED COLOSTRUM PROTEIN AND APPLICATION THEREOF

FIELD OF THE INVENTION

The present invention relates to a colostrum protein, and more particularly to a modified colostrum protein.

BACKGROUND OF THE INVENTION

Antibodies, also called immunoglobulins, are proteins secreted mainly by plasma cells and are used by immune systems to identify and neutralize pathogens such as bacteria and viruses. Antibodies include IgA, IgD, IgE, IgG and IgM, wherein IgA, which can be found in breast milk, saliva, tears and bronchial mucus, is very important for mucosal immunity acting as the first line of defense against foreign pathogens. Specifically, many pathogens can infect a host by the contact with mucosal surfaces of the respiratory, intestinal and genitourinary tract, and the secretory antibody IgA, is capable of binding to multiple antigenic determinants (epitope) of pathogens so that the pathogens cannot bind to mucosal cells to infect a host.

Animal husbandry plays an important role in the agricultural production, wherein the main cause of the poor pig reproduction is related to the high mortality rate in pigs. Generally, it is believed that obligate pathogen is the main cause of diseases in pigs wherein diseases with high mortality rates constitute the majority of pigs diseases. However, according to the result of a serology investigation performed at the graduate institute of veterinary pathobiology at National Chung Hsing University, there is no apparent outbreak of obligate pathogen diseases, e.g., swine fever or pseudorabies in pigs. Some illnesses in pigs caused by infection with single type of pathogen among pathogens with relatively low pathogenicity (e.g., mycoplasma, steurella and *salmonella*) are not severe. However, if pigs with low immunity are primarily and secondarily infected by a complex of the pathogens with relatively low pathogenicity, the synergistic effects of illnesses would cause the pigs death. Thus, pathogens with low pathogenicity have significant impacts on pig herds with low numbers of pigs.

Colostrum is a form of milk secreted by female mammals in the first 2-3 days after giving birth, and the milk secreted after the secretion of colostrum are transitional milk and mature milk. Colostrum contains five types of immunoglobulins which are IgA, IgD, IgE, IgG and IgM, wherein the IgG content is the highest. These immunoglobulins are crucial in defending against viral infection, bacterial infection, parasites and yeasts.

However, the beneficial ingredients in colostrum are rarely isolated effectively and used except for the lactoferrin, which is purified from colostrum and utilized, and is cultivated in transgenic animals. Moreover, due to the factors such as the short time period of colostrum secretion, the unstable protein in colostrums, and the difficulty of collecting and preserving the colostrums, there are still many difficulties in the practical application of colostrum even though the benefits of colostrums are numerous.

SUMMARY OF THE INVENTION

Thus, an object of the present invention is to provide a modified colostrum protein with improved stability in vitro, which can prevent and defend foreign pathogens.

The technical means adopted by the present invention to overcome the drawbacks in the prior art is to provide a modified colostrum protein, which is generated by replacing Ile at position 33, Glu at position 101 and Arg at position 175 present in the amino acid sequence of a wild type colostrum protein shown in SEQ ID NO.: 2 respectively with Ala, Cys and Cys.

In one embodiment of the present invention, a DNA encoding the amino acid sequence of the modified colostrum protein mentioned above is provided, and the DNA has a base sequence shown in SEQ ID NO.:3.

In one embodiment of the present invention, an oral dosage form comprising the modified colostrum protein mentioned above is provided.

In one embodiment of the present invention, an animal feed composition comprising the modified colostrum protein mentioned above is provided.

In one embodiment of the present invention, an animal feed composition is provided, wherein the modified colostrum protein is present in the animal feed composition in amount in a range from 0.01% to 0.02% by weight.

In one embodiment of the present invention, a pharmaceutical composition comprising a drug carrier and a vaccine adjuvant and the modified colostrum protein mentioned above is provided.

In one embodiment of the present invention, an application of the modified colostrum protein mentioned above to a preparation of a feed for enhancing the immune response in an animal is provided.

In one embodiment of the present invention, an application is provided, wherein the immune response in the animal is enhanced by increasing production of immunoglobulin A (IgA) of the animal.

In one embodiment of the present invention, an application of the modified colostrum protein mentioned above to a preparation of a feed to be administered to an animal is provided.

In one embodiment of the present invention, an application of the modified colostrum protein mentioned above to a preparation of a pharmaceutical composition to be administered to an animal is provided.

In one embodiment of the present invention, an application of the modified colostrum protein mentioned above to a preparation of a feed for preventing or treating a disease which can cause a mucosal immune response is provided.

In one embodiment of the present invention, the disease is porcine reproductive and respiratory syndrome (PRRS), foot-and-mouth disease (FMD), porcine epidemic diarrhea (PED) or avian influenza.

In one embodiment of the present invention, an application of the modified colostrum protein mentioned above to a preparation of a pharmaceutical composition for preventing or treating a disease which can cause a mucosal immune response is provided.

In one embodiment of the present invention, the disease is porcine reproductive and respiratory syndrome (PRRS), foot-and-mouth disease (FMD), porcine epidemic diarrhea (PED), avian influenza or human influenza.

By means of the technology of the present invention, the tertiary structure of the modified colostrums protein of the present invention is more stable compared with that of a wild type colostrum protein. Furthermore, the mixture of the modified colostrum protein and feed can increase the production of immunoglobulin IgA in pigs after being fed to pigs, and thus further prevent the infection in pigs with certain pathogens.

BRIEF DESCRIPTION OF THE DRAWINGS

FIG. 1 shows a separated colostrum protein associated with bacterial membrane;

FIG. 2 shows a colostrum serum from pigs containing PGRP;

DEDTAILED DESCRIPTION OF THE PREFERRED EMBODIMENTS

Figure 1:
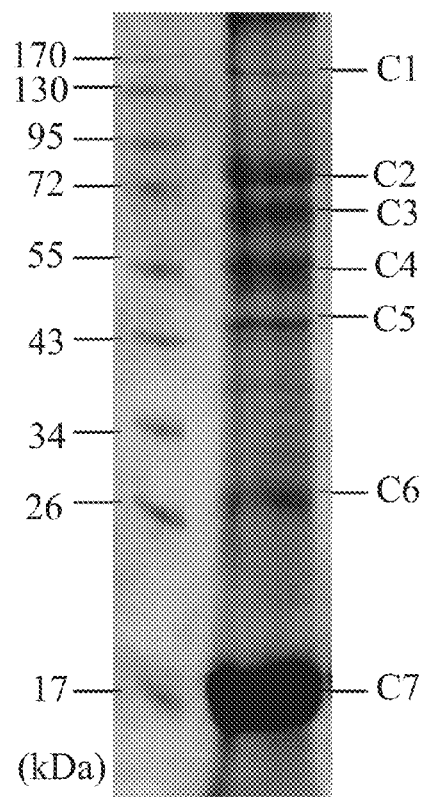

The preferred embodiments of the present invention are described below with reference to FIG. 1 to FIG. 8. The description is only the explanation of the preferred embodiments, and is not the limitation of the implementation of the present invention.

According to one embodiment of the present invention, the modified colostrums protein has an amino acid sequence shown in SEQ ID NO.: 1, which is generated by replacing Ile at position 33, Glu at position 101 and Arg at position 175 present in the amino acid sequence of a wild type colostrum protein shown in SEQ ID NO.: 2 respectively with Ala, Cys and Cys. The amino sequence of the modified colostrum protein is encoded by a DNA having a base sequence shown in SEQ ID NO.: 3.

Specifically, the modified colostrum protein of the present invention is obtained by purifying the protein associated with the peptidoglycan layer in the bacterial cell wall and modifying the base sequence thereof, and the modified colostrums protein is named Pathological Recognition Protein (PRP) after its characteristic.

Furthermore, the modified colostrums protein can be prepared in oral dosage form, e.g. solid oral dosage form, semi-solid oral dosage form, or liquid oral dosage form. Specifically, the solid oral dosage form can be a tablet, a multiparticulate, a powder, or a capsule.

Furthermore, an animal feed composition can be manufactured by combining the modified colostrums protein of the present invention with animal feed, wherein the animal feed composition comprises 0.01 wt % to 0.02 wt % the modified colostrums protein. Certainly, the present invention is not limited to this. In other embodiments, the percentage of the modified colostrums protein in the animal feed composition may differ depending on different situations.

Furthermore, the modified colostrum protein of the present invention can be applied to the preparation of a feed for enhancing the immune response in an animal, wherein the immune response in the animal is enhanced by increasing the production of immunoglobulin A (IgA) of the animal. Specifically, the animal can be a mammal, e.g. a pig or a cow.

Furthermore, the modified colostrum protein of the present invention can be applied to the preparation of a pharmaceutical composition to be administered to an animal, wherein the pharmaceutical composition comprises a drug for disease prevention, a drug carrier, and a vaccine adjuvant.

Furthermore, the modified colostrum protein of the present invention can be applied to the preparation of a pharmaceutical composition for preventing or treating avian influenza.

Furthermore, the modified colostrum protein of the present invention can be applied to the preparation of a pharmaceutical composition for preventing or treating human influenza.

Furthermore, the modified colostrum protein of the present invention can be applied to the preparation of a pharmaceutical composition for preventing or treating porcine reproductive and respiratory syndrome (PRRS).

Furthermore, the modified colostrum protein of the present invention can be applied to the preparation of a pharmaceutical composition for preventing or treating a disease which can cause a mucosal immune response.

In general, in this embodiment, pig colostrum is used as a sample which is analyzed using sodium dodecyl sulfate polyacrylamide gel electrophoresis (SDS-PAGE) method so as to purify the colostrum proteins within the pig colostrum associated with the peptidoglycan layer in the bacterial cell walls. In other embodiments, colostrum from other mammals can also be adopted as the analysis sample, e.g. cow colostrum. Next, the identification and properties of the peptidoglycan-associated proteins are analyzed via LC/MS/MS analysis and comparative genetic study, and the peptidoglycan-associated protein is named Pathological Recognition Protein, PRP. After the amino sequence of the PRP is obtained, the cloned pig pathological recognition protein gene is inserted into pYES2.1V5-His TOPO vector, and then the pYES2.1V5-His TOPO vector containing the cloned pathological recognition protein gene of pigs is used to transform yeast cells. The activity of the PRP is determined through the following processes: the evaluation of the in vitro expression level of the PRP; the fermentation test; intestinal bacterial flora analysis after mouse gavage; inhibition test of *Escherichia coli* and *Salmonella*, etc.

Purification of Protein:

Preparation of Gram-Positive Enhancer Matrix (GEM) particles: spotting *Lactococcus lactis* liquid under aseptic conditions; inoculating the *Lactococcus lactis* liquid into Difco™ Lactobacilli MRS Broth as culture medium; selecting a bacterial colony; picking one single bacterial strain and inoculating it into 25 ml MRS broth; carrying out cultivation under anaerobic condition for 18 hours at 37° C.; the culture medium containing the strain is split and transferred into 50 ml centrifugal tubes; centrifuging the centrifuge tubes at 13,000×g for 10 minutes; removing the supernatant and suspending clumps of bacteria with one-half the original volume of bacterial liquid of ddH$_2$O; centrifuging the centrifuge tubes at 13,000×g for 10 minutes and removing the supernatant; adding one-fifth the original volume of bacterial liquid of acid solution (0.6 M TCA, pH=1); releasing the caps and heating the centrifuge tubes in a water bath 30 minutes; centrifuging the centrifuge tubes at 13,000×g 10 minutes, removing the supernatant, and suspending the clumps of bacteria using with one-half the original volume of PBS; repeating the last step three times and centrifuging the centrifuge tubes at 13,000×g for 10 minutes; removing the supernatant; re-dissolving the clumps of bacteria with one-tenth the original volume bacterial liquid of PBS; counting the number of GEM particles per millimeter using a cytometer and finally, preserving the particles at −80° C. for future use.

Preparation of milk serum: apportioning obtained colostrums into 50 ml centrifuge tubes; centrifuging 30 minutes the centrifuge tubes at 10,000×g at 37° C. and then taking and transferring the sub-layer of the colostrum to another 50 ml centrifuge tube; adding 100% acetic acid, making the concentration of acetic acid 1%; leaving the samples in a constant temperature cabinet at 37° C. for 10 minutes in which acidification can be carried out; adding 1 M acetate of one-tenth the volume of the after the acidification to neutralize the colostrum; finally, pipetting the supernatant after 10 minutes of centrifugation at 10,000×g at 4° C. wherein the retrieved supernatant is milk serum. Bradford method is performed for the quantitative analysis of the prepared milk serum, which is preserved at −20° C. for future use.

Association of GEM particles and milk serum: mixing 100 μl of GEM particles and about 7 mg of milk serum; the mixture is placed on an oscillator to perform an oscillation of 30 minutes at room temperature; centrifuging the mixture for 10 minutes at 13,000×g; removing the supernatant; suspending the precipitate with 1 ml of PBS buffer and performing centrifugation at 13,000×g for 10 minutes; repeating the last step three times, and suspending again with 1 ml of elution buffer (containing 1 M NaCl); performing centrifugation at 13,000×g for 10 minutes, removing the supernatant, and re-dissolving the precipitate with 20 μl of PBS buffer; uniformly mixing the sample with sample buffer with a volume two times the volume of the sample; heating in a dry bath at 95° C. for 10 minutes; performing centrifugation at 13,000×g for 10 minutes; pipetting the supernatant and analyzing the supernatant with protein gel electrophoresis method.

Immunizing mouse: uniformly mixing 2.2×109 GEM particles with around 25 mg colostrum serum and oscillating the mixture; removing the supernatant after performing centrifugation at 13,000×g for 10 minutes; suspending the precipitate with 1 ml PBS buffer and performing centrifugation at 13,000×g for 10 minutes; repeating the last step three times; suspending the precipitate with 1 ml NaCl and performing centrifugation at 13,000×g for 10 minutes; removing the supernatant and re-dissolving the precipitate with 50 μl PBS buffer; adding protein sample buffer with a volume two times the original volume and uniformly mixing the sample buffer with the sample; heating at 95° C. in a dry bath for 10 minutes; performing centrifugation at 13,000×g for 10 minutes; pipetting and quantifying the upper layer with PBS buffer down to 100 μl; adding Freund's complete adjuvant of the same volume; mixing by oscillation at 4° C. for 12 hours, and the mixture is used for the primary immunizing injection. Afterwards, the Freund's incomplete adjuvant is used for emulsifying the antigenic protein. In the immunization test with antigen injection being immunizers, the immunization cycle is three weeks. For the first week, protein antigens mixed with Freund's complete adjuvant is used for abdominal immunizing injection in mice. Mouse blood samples were collected each week from mice's cheek using lancets, and the blood samples were used to prepare serum which is then preserved at −20° C. for future use. After the third immunization, mouse blood is obtained and used as the primary antibody of the Western blot method to detect the peptidoglycan-binding proteins in the colostrums serum. If the concentration of antibodies increases compared with that in the immunized serums collected after the primary immunization and the secondary immunization respectively, the fourth immunization injection of antigen proteins mixed with Freund's incomplete adjuvant is performed, and mouse whole blood is collected one week after.

Protein Western blot test: moistening PVDF membrane with anhydrous methanol for 15 minutes, and immersing the PVDF membrane in transfer buffer for future use; stacking absorbent cotton, filer paper, protein electrophoresis gel to be transferred, PVDF membrane, filter paper respectively on a transfer unit with avoidance of the formation of bubbles; filling the transfer unit with transfer buffer and cooling the transfer unit in an ice bath; performing transfer at a transfer voltage of 100 volt for one hour; immersing the PVDF membrane in TBS buffer containing 5% (w/v) of skimmed milk powder; shaking for at least two hours and pickling with TBS buffer for 5 minutes six times; the peptidoglycan-binding protein obtained from mouse immunized colostrum serum in the above-mentioned immunization test is used as an antibody probe; the peptidoglycan-binding proteins are dukyted 1000-fold with TBS buffer and shook to allow reaction with PVDF membrane at room temperature for one hour; pickling with TBS buffer for 5 minutes six times; the antibodies carrying Alkaline Phosphatase are used as secondary antibodies; the antibodies carrying Alkaline Phosphatase are diluted 1500-fold to serve as secondary antibodies and are shook to allow reaction with PVDF membrane at room temperature for one hour; pickling with TBS buffer for 5 minutes six times; finally, adding BCIP/NBT as liquid substrate for visualization; whenever the visualization is achieved, terminating the color reaction by cleansing two times.

Retrieval of Genes:

LC-MS/MS: LC-MS/MS is liquid chromatography (LC) in combination with tandem mass spectrometry (MS), which is used to analyze samples. LC-MS/MS utilizes the high analysis ability of liquid chromatography to separate mixtures containing polypeptide segments and then gasify the samples into ions using the primary ions in the mass spectrometry, which generates peptides of various sizes and electric charges that enter the first stage MS, in which the ions to be analyzed are fragmented by collisions with electrons or collision gas. In the second stage mass spectrometry, the mass to charge ratios (m/z) of sample fragments are measured by which the mass of substance to be analyzed can be derived given the amounts by which the ion fragments are charged. The amino acid sequences of the peptides separated by the liquid chromatography are obtained through ionization of two times, fragmentation, and at last genetic comparison. The corresponding genes are then obtained by performing DNA sequence comparison using biological information search software such as Mascot Analysis (Matrix Science, London, UK).

Gene cloning and activation analysis of pig pathological recognition protein: Amino acid sequence obtained from LC-MS/MS is used as the foundation of designing degenerate primers. The primer acts as a substitute together with Olgo-d(T) for pathological recognition protein gene in pig mammary gland cDNA. After RT-PCR, the fragments shown on the electrophoresis gel will be cloned one by one into TA-vectors. The complete pig pathological recognition protein genes, shown in SEQ ID NO.: 3, can be obtained by DNA sequencing and bioinformatic comparison. The cloned pig pathological recognition protein gene with modified sequence is first used to transform E. coli cells to induce the expression of the pathological recognition protein, and then the pathological recognition protein is purified. Whether the ability of the pathological recognition protein being combined with GEM particles still exists and stable after purification will be tested and analyzed using Western blotting after the purified pathological recognition proteins and GEM particles are combined.

Yeast transformation: to prevent the *E. coli* expression system from contaminating the pig-raising environment, yeast cells, which are already used in the feed, are used as carriers to express the pathological recognition protein. The cloned, modified, and sequenced pig pathological recognition protein genes are inserted into pYES2.1V5-His TOPO vectors (Invitrogen), a kind of yeast expression vectors, which are further introduced into yeast strains INVSc1. The original expression induction mechanism of this yeast expression system has been modified to start expressing the pathological recognition protein only when at certain range of temperature or at the existence of certain nutritive substances. However, since the technique has not yet applied for a patent, the information regarding the culture conditions is not disclosed herein.

Mouse Intestinal Microorganism Test:

The observation of intestinal bacterial flora: the pathological recognition protein is administered per mouse by oral gavage, with the weight of the protein being one-hundredth the weight of mice; performing oral gavage twice a day for six days, while the control group is only fed sterilized water of the same volume twice; mice were sacrificed and the small intestine (1.5 cm~2.5 cm below stomach) of each mouse is taken for analysis; the contents inside the mouse intestine are diluted at a proper dilution using sterilized PBS, and were cultured using culture bases; counting the number of bacterial strains after 24 hr. The bacterial flora is expressed in the log cfu of the bacterial strains. Moreover, the bacterial identification system API 20E is used for the identification of Enterobacteriaceae and Gram-negative bacteria, with the results are interpreted by table 1 below.

TABLE 1

| Test item | Result Negative | Positive | Note |
|---|---|---|---|
| ONPG | colorless | Yellow | |
| ADH | Yellow | Red/Orange | |
| LDC | Yellow | Red/Orage | |
| ODC | Yellow | Red/Orage | |
| CTT | Light Green/ Yellow | Blue-Green/ Green | |
| H2S | Colorless/Grey | Black precipitate | |
| URE | Yellow | Red/Orage | |
| TDA | Yellow | Dark Brown | |
| IND | Colorless/Pale Yellow-Green | Pink | Interpret after adding TDA |
| VP | colorless | Pink/Red | Interpret ten minutes after adding VP1 and VP2 |
| GEL | Melanin not diffuse | Melanin diffuse | |
| GLU | Blue/ Blue-Green | Yellow | |
| MAN | Blue/ Blue-Green | Yellow | |
| INO | Blue/ Blue-Green | Yellow | |
| SOR | Blue/ Blue-Green | Yellow | |
| RHA | Blue/ Blue-Green | Yellow | |
| SAC | Blue/ Blue-Green | Yellow | |

Fermentation test: transformed yeasts are cultivated in Winpact Bioreactor and Fermentor, and then the yeasts are first activated and suspended, and diluted according to OD value, and cultivated for 8 hours after the replacement of culture medium, during which variant factors such as temperature, rotational rate, pH value and dissolved oxygen are maintained in a constant range. Each patch of cultivated yeasts is sampled to analyze the expression of the pathological recognition protein. The yeasts in the fermentation broth are separated after eight hours of fermentation. 9 to 10 grams of recombinant yeasts can be obtained from about 1 liter of fermentation broth. The recombinant yeasts are then reserved in a dry environment for future use.

Purification of bacterial-membrane-binding protein and qualitative analysis of protein: the ways of foreign protein binding a cell membrane or a cell wall of a microorganism can be classified into five categories: (1) binding the cell membrane of a microorganism via the hydrophobic transmembrane domain of a transmembrane protein; (2) covalently binding the long chain fatty acid of a cell membrane by acetylation via the amino-terminal of a lipoprotein; (3) enabling proteins to stay on cell walls temporarily via LPCTG motif anchor, and covalently binding; (4) by non-covalent bindings between cell walls which exist in lysin motif (LysM) of various bacteria; and (5) by the bindings between the surface proteins of the foreign proteins and the surface proteins of the cell walls of microorganisms. The chromatographic column is stuffed with prepared GEM particles and is filled with colostrum, and the proteins combined with bacterial membrane are analyzed with SDS-PAGE method. In the SDS-PAGE test, it is found that there are more than one proteins that can be combined with bacterial membranes. After separating the proteins from bacterial membranes and sequencing the proteins, the proteins totaled seven, wherein one of them is lactoferrin, a known protein, and C7 is identified to be one of peptidoglycan recognition protein family. Please refer to C1~C7 in FIG. 1. (C7: RecName: Peptidoglycan recognition protein; Flags: Precursor, Nominal mass (Mr): 21024; Calculated pI value: 9.62 Variable modifications: Carbamidomethyl (C), Oxidation (M) Cleavage by Trypsin: cuts C-term side of KR unless next residue is P, Sequence Coverage: 11%)

Figure 2:
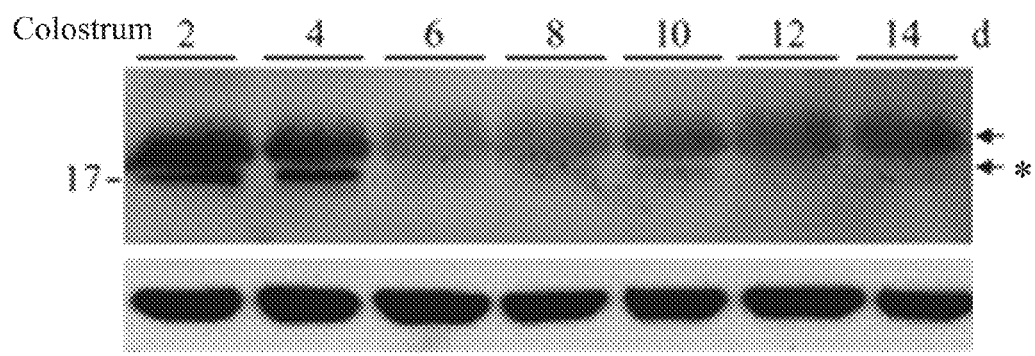
Figure 4:
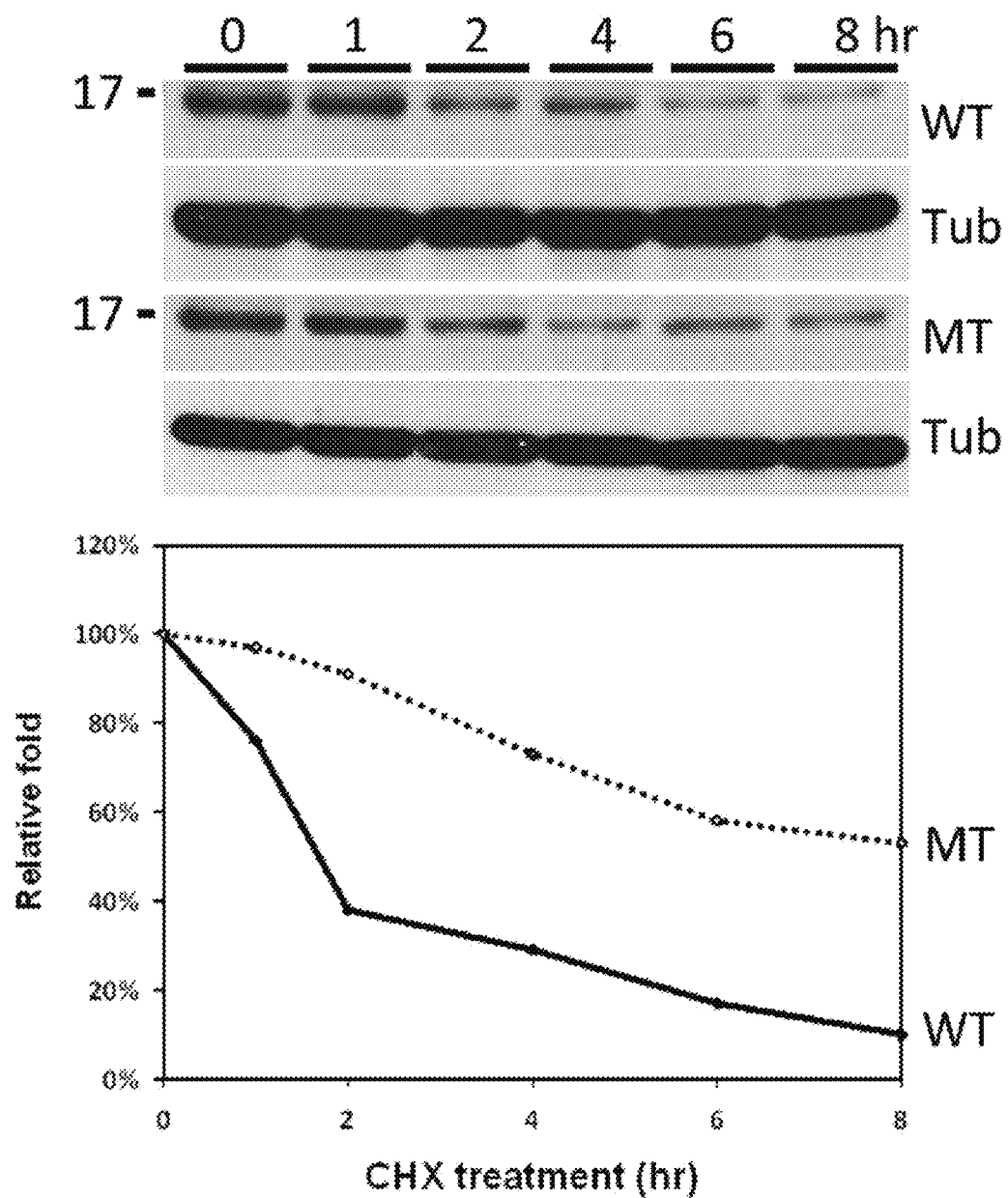
FIG. 4 shows a line graph illustrating a modified colostrums protein according to one embodiment of the present invention and a wild type colostrums protein processed by adding 50 μg/ml cycloheximide into the culture medium.

Due to the lack of PGRP antibodies in the market, in the present experiment, mice were injected with the purified C7 first in the abdomens, and then the immunized ascites is used to observe the expression of C7 protein in pig colostrums and mature milk. As shown in FIG. 2, which illustrates pig milk serum 2-4 days after labor, with * sign denoting PGRP with a molecular weight of 17 kDa, in our research, it is found that pig serum also contains PGRP, and that the amount of PGRP in the milk serum of pig colostrums is much higher than that in the milk serum of pig mature milk. However, in the process of the present experiment, it is also found that the C7 protein is extremely unstable. After two days of preservation at −20° C., the C7 protein in the sample will disappear. The instability restrains the C7 protein from being applied to the related industries. Hence, in the follow-up embodiments, the C7 protein is modified so as to stabilize the tertiary structure of the C7 protein, and the C7 protein is named pathological recognition protein, PRP, after its characteristics, i.e. the modified colostrum protein of the present invention, which is shown in FIG. 4.

Figure 3:
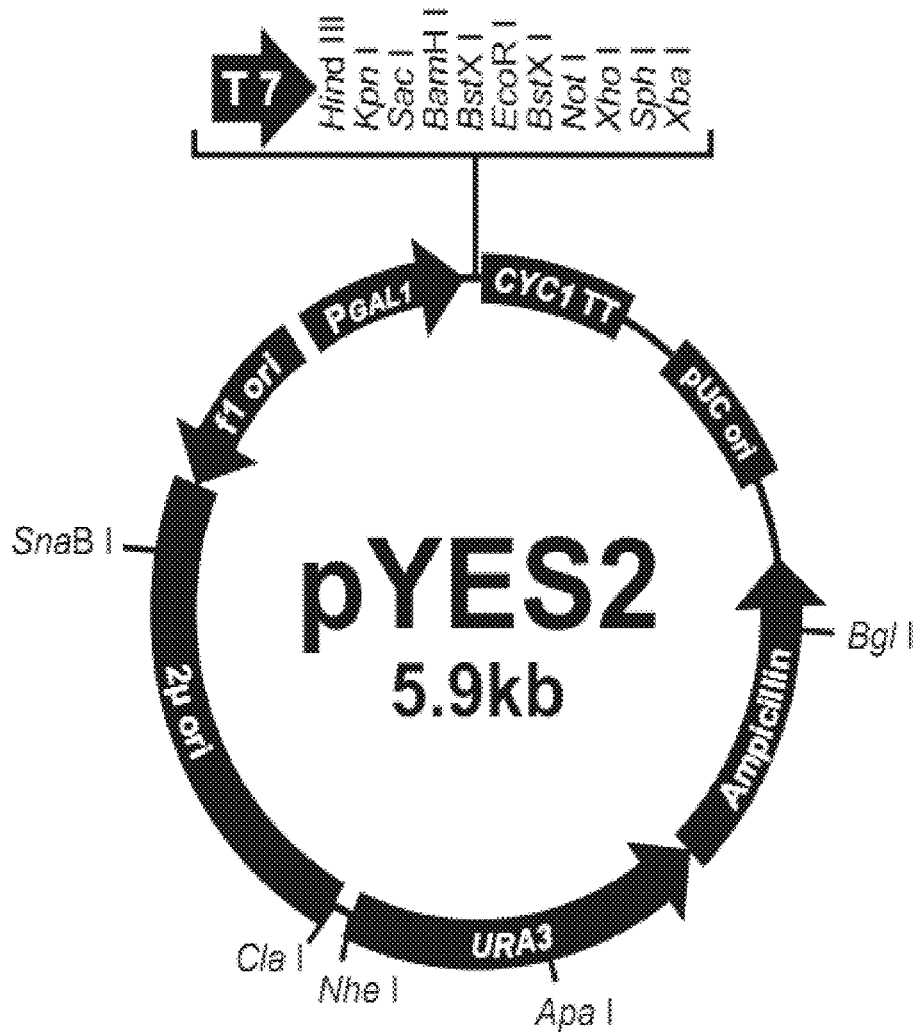
FIG. 3 illustrates a pig pathological recognition protein expressed in a yeast expression system.
Figure 5:
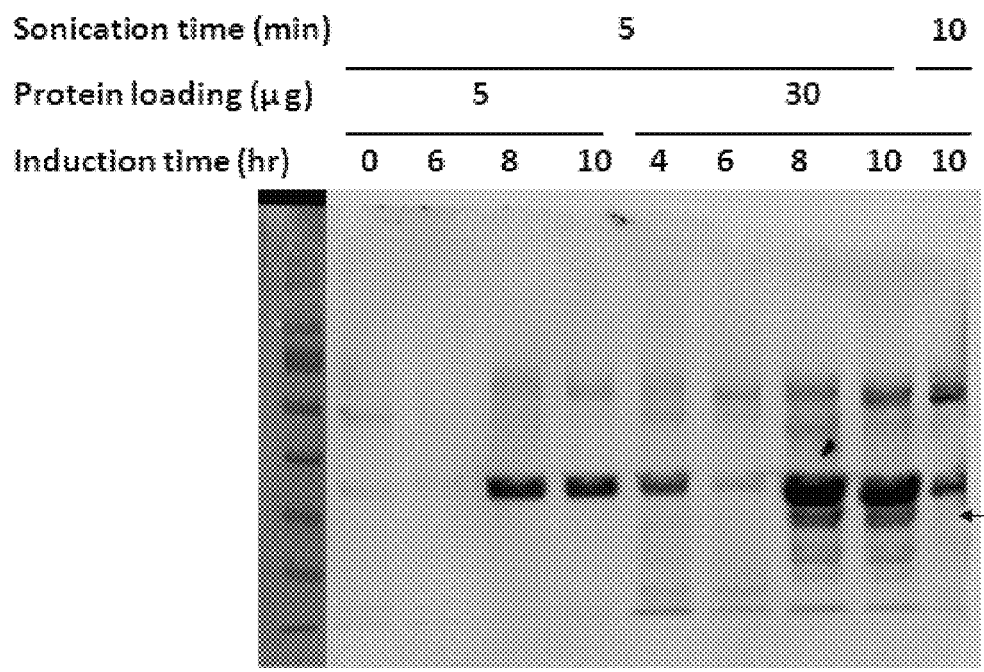
FIG. 5 shows a result of a western blot analysis of the modified colostrums protein according to one embodiment of the present invention.

Pig pathological recognition protein cloning, yeast transformation and production rate monitoring: according to the former experience in the use of recombinant protein by developers, although recombinant protein with market value can be developed in laboratories, the production of the recombinant proteins with market value is hard to be realized due to some difficulties such as the expression level, stability, and production cost of protein. Take into consideration the above problems, the pig pathological recognition protein gene is used to transform yeast cells. Although the culture conditions are difficult to determine, yeast cells are used to express the pig pathological recognition protein (as shown in FIG. 3) because yeast cells are beneficial in commercial use. The pig pathological recognition protein can be steadily expressed now after the change in recipe formulation, temperature, oxygen dissolution rate, and fermentation time for several times. The monthly yield is 280 tons pig feed. One millimeter of the feed is sampled before it is fermented, and after the fermentation the feed is sampled again. The samples are analyzed using Western blotting to determine the performance and yield of the pathological recognition protein. FIG. 5 shows the result of protein expression monitoring based on one fermentation. As shown in FIG. 5, the analysis on the samples collected at different time points were analyzed and show that the sample which has gone through 8 hour fermentation performs the best expression level, as the arrow at 17 kDA indicated. Such monitoring is performed right after the end of each fermentation to confirm if the fermentation condition and the strain are in the best states. The yeasts collected after the fermentation are centrifuged, and the supernatant is removed afterwards, and the solid matter is frozen right away at −50° C. and dried, after which it is preserved with avoidance of humidity. Before being mixed with other components in feed, the preserved yeasts are first mixed with feed substrates.

Figure 6:
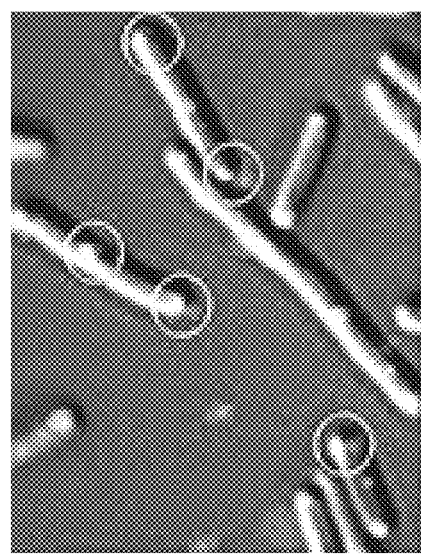
FIG. 6 shows an electron-microscopy observation of the modified colostrums protein according to one embodiment of the present invention being mixed with *Escherichia coli*.
Figure 7:
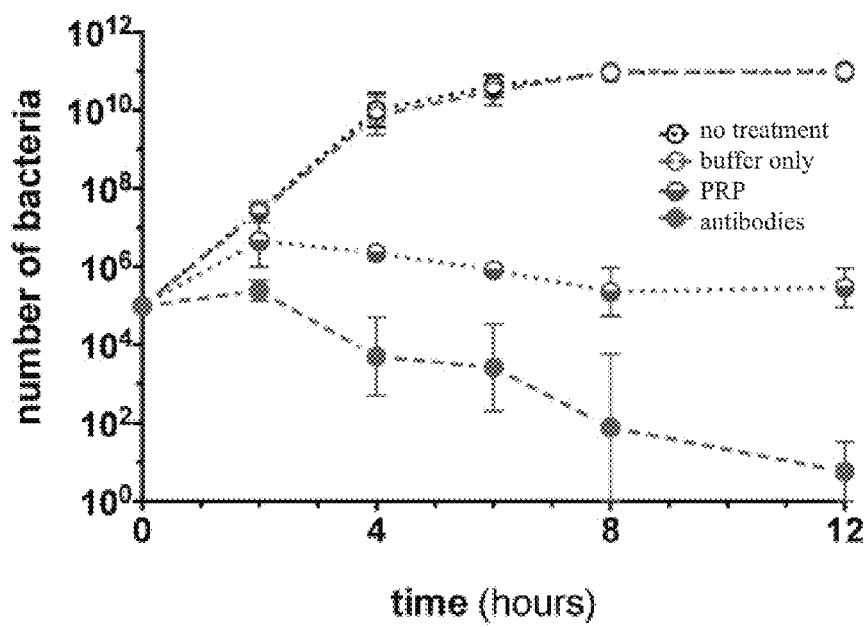
FIG. 7 is a line graph illustrating the bacterial population in mice after the modified colostrums protein according to the present invention is administered to the mice by gavage.
Figure 8:
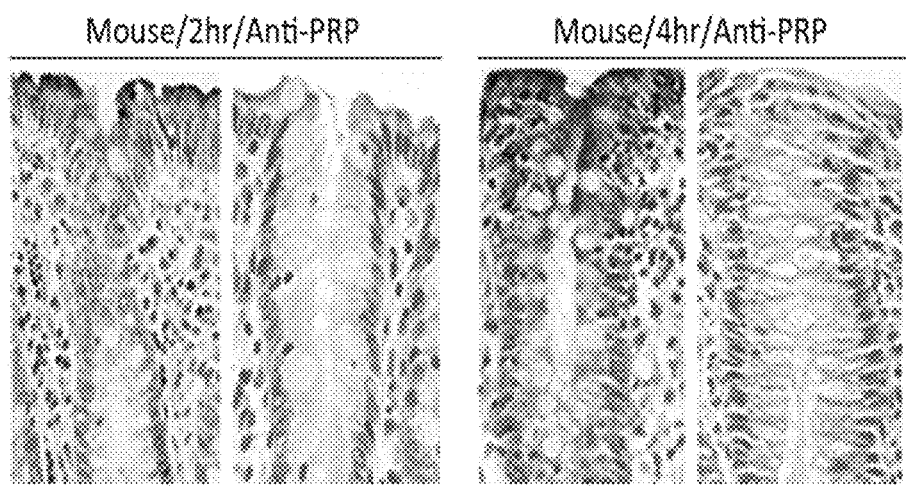
FIG. 8 illustrates immunohistochemical staining of mouse intestine after the modified colostrums protein is administered to a mouse.

Please refer to FIG. 6 to FIG. 8. ICR (Institute for Cancer Research) strain mice were administered by gavage once per two days pathological recognition protein weighing one-hundredth of the weight of each mouse. The duration of the administration is six days in total. The control group is fed sterilized water of the same volume twice. After the experiment, the animals are sacrificed, and the small intestines (1.5-2.5 cm below the stomach) of the animals are sampled for analysis. In each experiment, the experimental group and the control group each contain 25 animals. If there's any animal dies during the experiments due to gavage, the data of the dead animal will be deleted. The total amount of bacteria in the experimental group, i.e. the group fed the pathological recognition protein, is 50% less than the amount of bacteria in the control group. As shown in FIG. 7, the blue curve is the experiment group with mice fed PRP, and when time passes by the PRP inhibits the growth of bacteria by 50 percent. From the result of the identification of the bacterial flora, the inhibited bacteria are mostly Gram-positive bacteria. Besides, since the pathological recognition protein has the characteristic of adhering to bacterial membrane, in this experiment, purified yeasts transformed by the pathological recognition proteins are mixed with E. coli. After replacing the culture medium two times, the E. coli is observed under electron microscope to determine whether there are pathological recognition proteins binding to the E. coli, as shown in FIG. 6, wherein the circled parts are where the bindings happen.

The following are administration tests of the mixture of modified colostrum protein and animal feed to young pigs:

Contemporary comparison: 16 four-week-old young pigs are grouped into two groups and are kept in two adjacent pigsties; collecting bloods to examine the titre of the antibodies against PRRS (IgG); collecting bloods to examine the titre of the antibodies against PRRS (IgG) after adding 0.02% of PRP into the feed.

Result: Table 2 shows negative results for IgG in the both the experimental group and the control group before the experiment. However, the results of IgG tests remain negative in the experiment group which receives PRP addition when the pigs are of eight-week-old while the results of IgG tests are all positive in the control group. The above results prove that PRP can increase the production of immunoglobulin IgA, which neutralizes PRRS virus with a tendency to penetrate through mucosa tissue of pigs and to further activate the lymphatic system to produce IgG The neutralization of PRRS virus takes places in the mucosa tissue.

TABLE 2

IgG test in four-week-old pigs:

| No. | Experimental Group | Control Group |
|---|---|---|
| 1 | 0.019 | 0.126 |
| 2 | 0.010 | 0.084 |
| 3 | 0.000 | 0.015 |
| 4 | 0.014 | 0.077 |
| 5 | 0.008 | 0.065 |
| 6 | 0.000 | 0.081 |
| 7 | 0.000 | 0.112 |
| 8 | 0.008 | 0.090 |

Note:
Result of antibody titre lower than 0.4 is determined to be negative.

TABLE 3

IgG test in eight-week-old pigs:

| No. | Experimental Group | Control Group |
|---|---|---|
| 1 | 0.000 | 0.964 |
| 2 | 0.000 | 1.341 |
| 3 | 0.000 | 1.866 |
| 4 | 0.000 | 1.584 |
| 5 | 0.000 | 1.169 |
| 6 | 0.000 | 1.761 |
| 7 | 0.000 | 1.621 |
| 8 | 0.000 | 1.498 |

Note:
Result of antibody titre lower than 0.4 is determined to be negative.

What is claimed is:

1. A modified colostrum protein having an amino acid sequence shown in SEQ ID NO.: 1, which is generated by replacing Ile at position 33, Glu at position 101 and Arg at position 175 present in the amino acid sequence of a wild type colostrum protein shown in SEQ ID NO.: 2 respectively with Ala, Cys and Cys.

2. A DNA encoding the amino acid sequence of the modified colostrum protein according to claim 1, the DNA having a base sequence shown in SEQ ID NO.: 3.

3. A pharmaceutical composition, comprising:
a drug carrier and a vaccine adjuvant, and
the modified colostrum protein according to claim 1.

* * * * *

SEQUENCE LISTING

<160> NUMBER OF SEQ ID NOS: 3

<210> SEQ ID NO 1
<211> LENGTH: 196
<212> TYPE: PRT
<213> ORGANISM: human

<400> SEQUENCE: 1

Met Ser Arg Arg Ser Met Leu Leu Ala Trp Ala Leu Pro Ser Leu Leu

```
1               5                    10                   15
Arg Leu Gly Ala Ala Gln Glu Thr Glu Asp Pro Ala Cys Cys Ser Pro
                20                  25                  30

Ala Val Pro Arg Asn Glu Trp Lys Ala Leu Ala Ser Glu Cys Ala Gln
                35                  40                  45

His Leu Ser Leu Pro Leu Arg Tyr Val Val Ser His Thr Ala Gly
     50                  55                  60

Ser Ser Cys Asn Thr Pro Ala Ser Cys Gln Gln Gln Ala Arg Asn Val
65                  70                  75                  80

Gln His Tyr His Met Lys Thr Leu Gly Trp Cys Asp Val Gly Tyr Asn
                    85                  90                  95

Phe Leu Ile Gly Cys Asp Gly Leu Val Tyr Glu Gly Arg Gly Trp Asn
                100                 105                 110

Phe Thr Gly Ala His Ser Gly His Leu Trp Asn Pro Met Ser Ile Gly
                115                 120                 125

Ile Ser Phe Met Gly Asn Tyr Met Asp Arg Val Pro Thr Pro Gln Ala
            130                 135                 140

Ile Arg Ala Ala Gln Gly Leu Leu Ala Cys Gly Val Ala Gln Gly Ala
145                 150                 155                 160

Leu Arg Ser Asn Tyr Val Leu Lys Gly His Arg Asp Val Gln Cys Thr
                165                 170                 175

Leu Ser Pro Gly Asn Gln Leu Tyr His Leu Ile Gln Asn Trp Pro His
                180                 185                 190

Tyr Arg Ser Pro
            195

<210> SEQ ID NO 2
<211> LENGTH: 196
<212> TYPE: PRT
<213> ORGANISM: human

<400> SEQUENCE: 2

Met Ser Arg Arg Ser Met Leu Leu Ala Trp Ala Leu Pro Ser Leu Leu
1               5                   10                  15

Arg Leu Gly Ala Ala Gln Glu Thr Glu Asp Pro Ala Cys Cys Ser Pro
                20                  25                  30

Ile Val Pro Arg Asn Glu Trp Lys Ala Leu Ala Ser Glu Cys Ala Gln
                35                  40                  45

His Leu Ser Leu Pro Leu Arg Tyr Val Val Ser His Thr Ala Gly
     50                  55                  60

Ser Ser Cys Asn Thr Pro Ala Ser Cys Gln Gln Gln Ala Arg Asn Val
65                  70                  75                  80

Gln His Tyr His Met Lys Thr Leu Gly Trp Cys Asp Val Gly Tyr Asn
                    85                  90                  95

Phe Leu Ile Gly Glu Asp Gly Leu Val Tyr Glu Gly Arg Gly Trp Asn
                100                 105                 110

Phe Thr Gly Ala His Ser Gly His Leu Trp Asn Pro Met Ser Ile Gly
                115                 120                 125

Ile Ser Phe Met Gly Asn Tyr Met Asp Arg Val Pro Thr Pro Gln Ala
            130                 135                 140

Ile Arg Ala Ala Gln Gly Leu Leu Ala Cys Gly Val Ala Gln Gly Ala
145                 150                 155                 160

Leu Arg Ser Asn Tyr Val Leu Lys Gly His Arg Asp Val Gln Arg Thr
                165                 170                 175
```

```
Leu Ser Pro Gly Asn Gln Leu Tyr His Leu Ile Gln Asn Trp Pro His
            180                 185                 190
Tyr Arg Ser Pro
        195

<210> SEQ ID NO 3
<211> LENGTH: 590
<212> TYPE: DNA
<213> ORGANISM: human

<400> SEQUENCE: 3
atgtcccgcc gctctatgct gcttgcctgg gctctcccca gcctccttcg actcggagcg         60
gctcaggaga cagaagaccc ggcctgctgc agccccgccg tgccccggaa cgagtggaag        120
gccctggcat cagagtgcgc ccagcacctg agcctgccct tacgctatgt ggtggtatcg        180
cacacggcgg gcagcagctg caacaccccc gcctcgtgcc agcagcaggc ccggaatgtg        240
cagcactacc acatgaagac actgggctgg tgcgacgtgg gctacaactt cctgattgga        300
tgcgacgggc tcgtatacga gggccgtggc tggaacttca cgggtgccca ctcaggtcac        360
ttatggaacc ccatgtccat tggcatcagc ttcatgggca actacatgga tcgggtgccc        420 acacccagg ccatccgggc agcccagggt ctactggcct gcggtgtggc tcagggagcc        480
ctgaggtcca actatgtgct caaaggacac cgggatgtgc agtgcacact ctctccaggc        540
aaccagctct accacctcat ccagaattgg ccacactacc gctcccctg                    590
```